US012597502B2

(12) United States Patent
Lamoncha

(10) Patent No.: US 12,597,502 B2
(45) Date of Patent: Apr. 7, 2026

(54) DEVICES, SYSTEMS, METHODS FOR FACILITATING INTERMITTENT FUELING OR OTHER DIETARY PLAN ADHERENCE

(71) Applicant: Mark Lamoncha, Columbiana, OH (US)

(72) Inventor: Mark Lamoncha, Columbiana, OH (US)

( * ) Notice: Subject to any disclaimer, the term of this patent is extended or adjusted under 35 U.S.C. 154(b) by 586 days.

(21) Appl. No.: 18/145,060

(22) Filed: Dec. 22, 2022

(65) Prior Publication Data

US 2024/0212823 A1     Jun. 27, 2024

(51) Int. Cl.
*G16H 20/60*          (2018.01)
*G16H 10/20*          (2018.01)

(52) U.S. Cl.
CPC ............. *G16H 20/60* (2018.01); *G16H 10/20* (2018.01)

(58) Field of Classification Search
CPC ............................... G16H 20/60; G16H 10/20
See application file for complete search history.

(56) References Cited

U.S. PATENT DOCUMENTS

| | | | | |
|---|---|---|---|---|
| 5,323,921 A | * | 6/1994 | Olsson ................... | B65D 45/24 |
| | | | | 220/6 |
| 7,212,098 B1 | * | 5/2007 | Trent ................. | G07C 9/00912 |
| | | | | 340/568.1 |
| 11,345,528 B2 | * | 5/2022 | Leary ................. | A47G 19/2272 |
| 2015/0093725 A1 | * | 4/2015 | Baarman ................. | G09B 5/00 |
| | | | | 600/300 |
| 2018/0127180 A1 | * | 5/2018 | Gordon .............. | B65D 81/2038 |
| 2020/0399021 A1 | * | 12/2020 | Green ................ | B65D 21/0233 |

FOREIGN PATENT DOCUMENTS

| | | | | | |
|---|---|---|---|---|---|
| GB | | 2604739 A | * | 9/2022 | ............. G16H 20/60 |
| WO | WO-2022172008 A1 | * | 8/2022 | | ............. G07F 11/54 |

* cited by examiner

*Primary Examiner* — Jacques M Saint Surin
(74) *Attorney, Agent, or Firm* — Standley Law Group LLP; Jeffrey S. Standley; Adam J. Smith

(57)          ABSTRACT
Devices, such as containers, systems, and methods for facilitating intermittent fueling, or adherence to other dietary plans or programs, are provided. The containers may include a moveable access panel, a locking mechanism configured to selectively secure the access panel in a closed position, and a controller configured to receive user input regarding dietary plan preferences and operate the locking mechanism in accordance with the user input. The container may be programmed locally or by way of a remote server. Locking operations may be modified according to consumption and activity information.

19 Claims, 6 Drawing Sheets

Number of meals
- Meal time
- Calorie apportionment

User activity
- Caloric intake
  - Type of food
  - Amount of food
- Caloric output
  - Type of activity
  - Amount of activity Container Updates
- Container 1 – type of food
- Container 2 – type of food
- Container 3 – type of food

44B

36

DEVICES, SYSTEMS, METHODS FOR FACILITATING INTERMITTENT FUELING OR OTHER DIETARY PLAN ADHERENCE

CROSS-REFERENCE TO RELATED APPLICATIONS

This application is filed as original and makes no priority claim.

TECHNICAL FIELD

Exemplary embodiments relate generally to devices, systems, and methods for facilitating intermittent fueling, or adherence to other dietary plans or programs.

BACKGROUND AND SUMMARY OF THE INVENTION

A variety of known dietary techniques are known. Fundamentally, however, many dietary techniques involve limiting caloric intake against caloric output. One such dietary technique, by way of non-limiting example, is intermittent fasting, whereby an individual elects to only eat during certain periods of the day. By limiting the time window in which one has to eat, one generally consumes less calories overall, often leading to a caloric deficit and thus achieving weight loss. Other dietary plans, by way of example, include only eating certain types of food, limiting caloric intake, increasing caloric intake (e.g., for weight or muscle gain), or the like. A wide variety of dietary techniques have been established over the years.

Various factors may affect the ideal time, type, and/or amount of food one should consume to achieve various dietary goals. Sometimes, difficulties arise in mental willpower to resist the urge to eat outside of these ideal eating times, types of food, and/or amounts of food.

Devices, such as containers, systems, and methods for facilitating intermittent fueling, or adherence to other dietary plans or programs, are provided. Programmable, lockable containers may be utilized. The containers may only be unlocked certain times of day, such as to facilitate intermittent fueling plan adherence.

Alternatively, or additionally, other dietary plans such as caloric surplus or deficit may be programmed and facilitated. Estimated caloric intake may be determined, such as from weight readings of the containers in conjunction with reported types of food, activity of smart utensils, activity of wrist mounted devices, weight readings in footwear, and/or user reported intake or output. Estimated caloric output may be determined, such as from activity of wrist mounted devices, activity of personal electronic devices, user reported activity, activity of footwear, and/or baseline estimated output. The containers may be unlocked until dietary goals are met, and then may be locked. Caloric intake may be apportioned into meals throughout the day.

In exemplary embodiments, without limitation, intermittent fueling programs may be capped by caloric goals. For example, without limitation, the containers may be programmed to operate based on time of day unless and until certain estimated net caloric surplus or deficits are reached, and the programming may be adjusted.

Further features and advantages of the systems and methods disclosed herein, as well as the structure and operation of various aspects of the present disclosure, are described in detail below with reference to the accompanying figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Embodiments of the invention are described herein with reference to illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Figure 1:
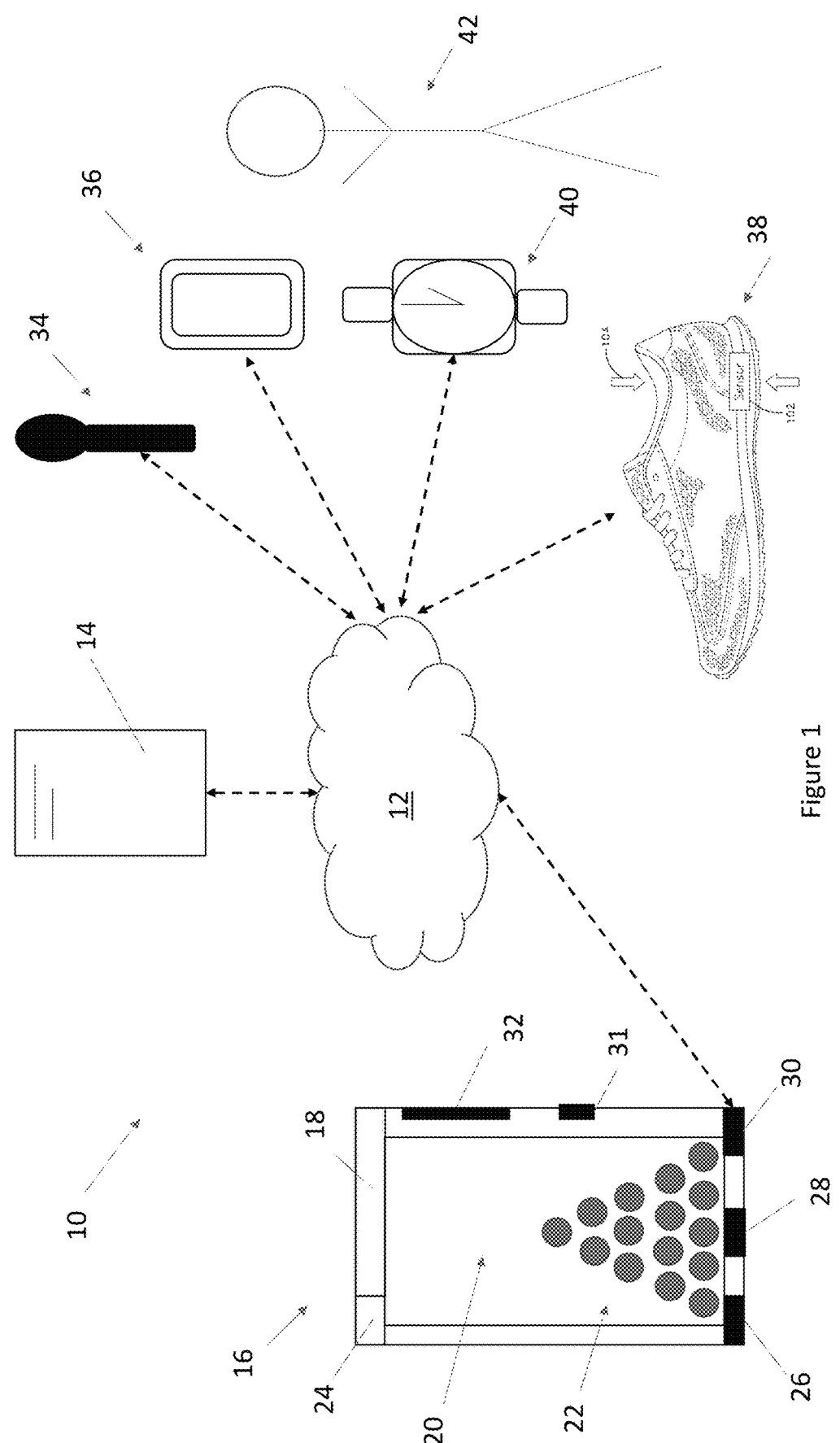
FIG. 1 is a plan view of an exemplary system for facilitating intermittent fueling and other dietary plans.

FIG. 1 illustrates a system 10 for facilitating intermittent fueling, or other dietary plan adherence. The system 10 may comprise one or more containers 16. The containers 16 may be a selective lockable, such in an electronically programmable fashion. The system 10 may comprise one or more servers 14. The system 10 may comprise one or more smart utensils 34. The system 10 may comprise one or more personal electronic devices 36. The system 10 may comprise one or more wrist mounted devices 40. The system 10 may comprise one or more items of footwear 38 with integrated sensor(s) 102. The container(s) 16, smart utensil(s) 34, personal electronic device(s) 36, wrist mounted device(s) 40, and/or footwear 38 may be in electronic communication with the server(s) 14 and/or one another by way of one or more networks 12. The network(s) 12 may comprise one or more internets, intranets, near field communication networks, the world wide web, cellular networks, combinations thereof, or the like. The server(s) 14 may be configured to host one or more software applications executed, at least in part, on one or more of the container(s) 16, smart utensil(s)

34, personal electronic device(s) 36, wrist mounted device(s) 40, and/or footwear 38, by way of non-limiting example.

The container(s) 16 may be configured for selective locking. Each of the containers 16 may include an access panel 18, such as a lid. A locking mechanism 24 may be controlled to prevent opening of the access panel 18 when engaged. The locking mechanism 24 may be electronically controlled, such as by way of one or more controllers 26. Opening of the access panel 18 may permit access to an interior compartment 20 for housing foodstuffs 22.

One or more sensors 28 may be provided at the containers 16. The sensors 28 may comprise, for example, without limitation, load cells configured to measure weight of the container 16. The sensor(s) 28 may be in electronic communication with the controller(s) 26. Alternatively, or additionally, the sensor(s) 28 may comprise optical sensors, balances, scales, combinations thereof, or the like.

The controllers 26 may be configured to take measurements before and after foodstuffs 22 are added to the containers 16, such as to determine an amount of foodstuffs 22 present in the container, by way of non-limiting example. As another example, without limitation, the controllers 26 may be configured to take measurements before and after foodstuffs 22 are removed from the container, such as to demine an amount of foodstuffs 22 removed, and therefore presumably consumed by the user 42. The containers 16 may be configured to record when the access panel 18 is opened and/or closed, such as by way of one or more sensors.

In exemplary embodiments, without limitation, some or all of the containers 16 may comprise separate compartments, such as formed by one or more dividers. Each of the compartments may be associated with one or more sensors 28, such that readings for the whole container 16 and/or separate compartments thereof, may be separately obtained. For example, without limitation, separate sensors 28 may be provided for each compartment such that independent weight readings for each compartment may be obtained.

The containers 16 may comprise one or more user interfaces 32, such as electronic displays, keypads, touchscreens, keys, locks, combinations thereof, or the like. The user interfaces 32 may permit user 42 programming of the containers 16. The user interfaces 32 may be in electronic communication with the controllers 26.

By way of non-limiting example, user 42 input at the user interfaces 32 may include types of foodstuffs 22 in the container 16, intent to add foodstuffs 22 to the containers 16, intent to remove foodstuffs 22 from the container 16, codes for unlocking the container 16, codes for locking the container 16, dietary preferences, times for locking the container 16, times for unlocking the container 16, user 42 information (login, profile, height, weight, sex, dietary goals, etc.), user 42 overrides, combinations thereof, or the like. User 42 overrides may, alternatively or additionally be provided by way of a keyed lock of combination lock, by way of non-limiting example. Dietary goals and/or preferences may include, for example, without limitation, times of day for eating/not eating (intermittent fueling/fasting), caloric maintenance, surplus, or deficit goals, daily caloric goals, weight goals, combinations thereof, or the like. The container(s) 16 may comprise, or be in communication with, one or more timing devices, such as clocks.

The controllers 26 may be in electronic communication with one or more network connectivity devices 30, such as, but not limited to, wireless routers, near field communication devices, modems, combinations thereof, or the like. The network connectivity device(s) 30 may be configured to facilitate communication with the network(s) 12.

In exemplary embodiments, the containers 16 and/or compartments therein may be sized, shaped, and/or otherwise configured to accommodate certain types or kinds of foods and/or portion sizes. For example, without limitation, the containers 16 may be uninsulated, insulated, sealable, unsealed, ventilated, made with particular material, combinations thereof, or the like. As another example, without limitation, the containers 16 and/or compartments may be sized to accept only specific, estimated caloric amounts of certain types of food (e.g., 300 calorie snack containers, 1000 calorie meal containers, etc.). The containers 16 may be configured for microwave, dishwasher, and/or refrigerator use. The containers 16 may be provided in any size and/or shape. Any number of containers 16 may be utilized of a same or different size, shape, and/or type.

The smart utensils 34, wrist mounted devices 40, personal electronic devices 36, and/or footwear 38, and/or components related to the same, may be as shown and/or described in U.S. Pat. No. 11,302,216 issued Apr. 12, 2022 (the "'216 Patent"), the disclosures of which are hereby incorporated by reference as if fully restated herein. In exemplary embodiments, without limitation, certain features or aspects of the server(s) 14 and/or related software applications may be as shown and/or described in the '216 Patent. The smart utensils 34, wrist mounted devices 40, personal electronic devices 36, and/or footwear 38 may comprise components shown and/or described in the '216 Patent in exemplary embodiments, without limitation.

Each of the smart utensils 34, wrist mounted devices 40, personal electronic devices 36, and/or footwear 38 may comprise one or more network communication devices for facilitating communication with the server(s) 14, the container(s) 16, and/or one another, such as by way of the networks 12. The smart utensils 34 may comprise any type of kind of utensil (e.g., spoon, fork, spork, knife, etc.). The wrist mounted devices 40 may comprise any type or kind of device intended for wrist mounting (e.g., watch, bracelet, band, etc.). The personal electronic devices 36 may comprise any type or kind of smartphone, tablet, e-reader, personal computer, augmented reality device, smart device, combinations thereof, or the like. As used herein, the term smart may denote the ability to communicate electronically, such as in a wireless manner, with at least some other component of the system 10, and may include necessary equipment for facilitating the same.

The footwear 38 may comprise any type or kind of footwear (e.g., shoes, sandals, boots, etc.). Sensors 102 may be provided in some or all of the footwear 38 and may be embedded in the footwear or a removable insole such that it may be interchanged with and/or used in other footwear 38. The sensors 102 may comprise load cells, temperature sensors, moisture sensors, pressure sensors, combinations thereof, or the like. Any type, kind, and/or number of sensors 102 may be utilized. The footwear 38 may be confirmed for electronic communication, such as in a wireless manner, with at least some other component of the system 10, such as, but not limited to, the server(s) 14, and may include necessary equipment for facilitating the same.

In exemplary embodiments, without limitation, the footwear 38 and/or insoles thereof, may comprise one or more thermally absorption materials. For example, without limitation, the footwear 38 and/or insoles thereof may comprise one or more air pockets and/or gels. These air pockets and/or gels may be configured to absorb thermal energy from the wearer. Sensors 102, such as, but not limited to, temperature sensors, may be located at least partially within, or otherwise in thermal communication with, these air pockets and/or gels. Alternatively, or additionally, the sensors 102 may comprise pressure sensors configured to measure changes in pressure at the air pockets and/or gels. Temperatures, pressures, or other data points and/or changes may be measured by the sensors 102 and/or reported to the system 10, such as, but not limited to, the server(s) 14. Temperature and/or pressure changes may be indicative of caloric burning activity, by way of non-limiting example. For example, without limitation, increased or decreased temperatures may be associated with certain metabolic activity, aerobic activity, combinations thereof, or the like. As another example, without limitation, pressure changes may indicate aerobic activity (e.g., walking, jogging).

Some or all of the containers 16 may comprise one or more identifiers 31. The identifiers 31 may comprise, for example, without limitation, optically readable code (e.g., alphanumeric, bar codes, QR codes, etc.), near field communication device (e.g., RFID tags), combinations thereof, or the like. The identifiers 31 may be configured to provide certain identifying information to the one or more personal electronic devices 36, such as automatically and electronically, by optical scanning or wireless communication.

Figure 2:
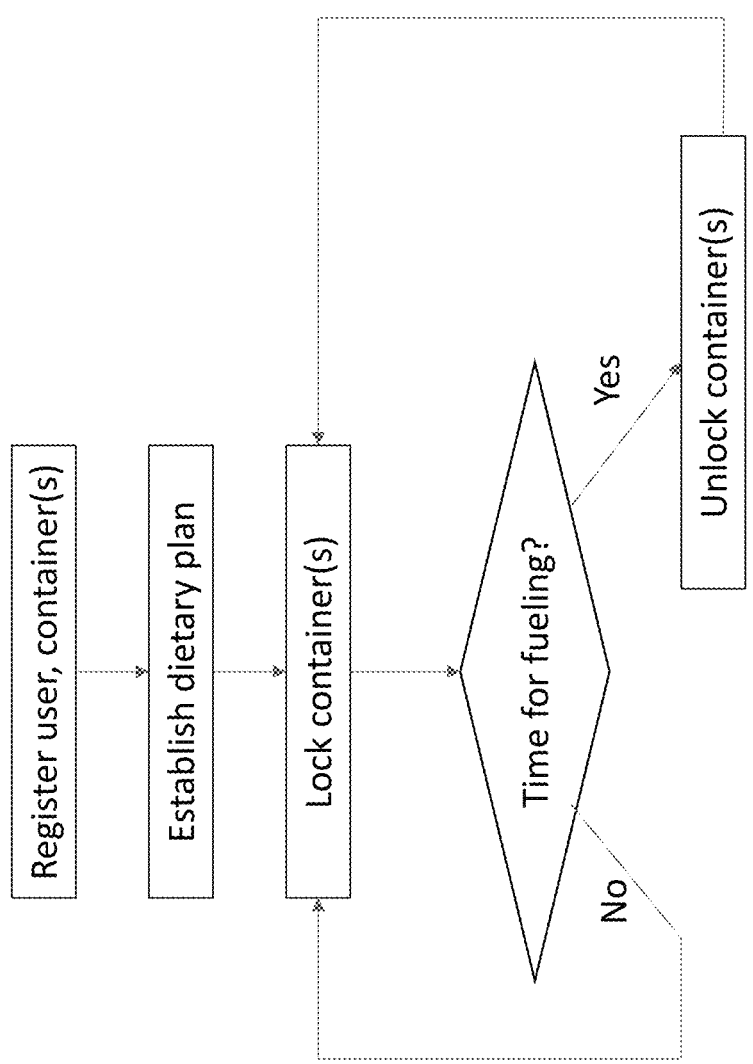
FIG. 2 is a flow chart with exemplary logic for using the system of FIG. 1.
Figure 3:
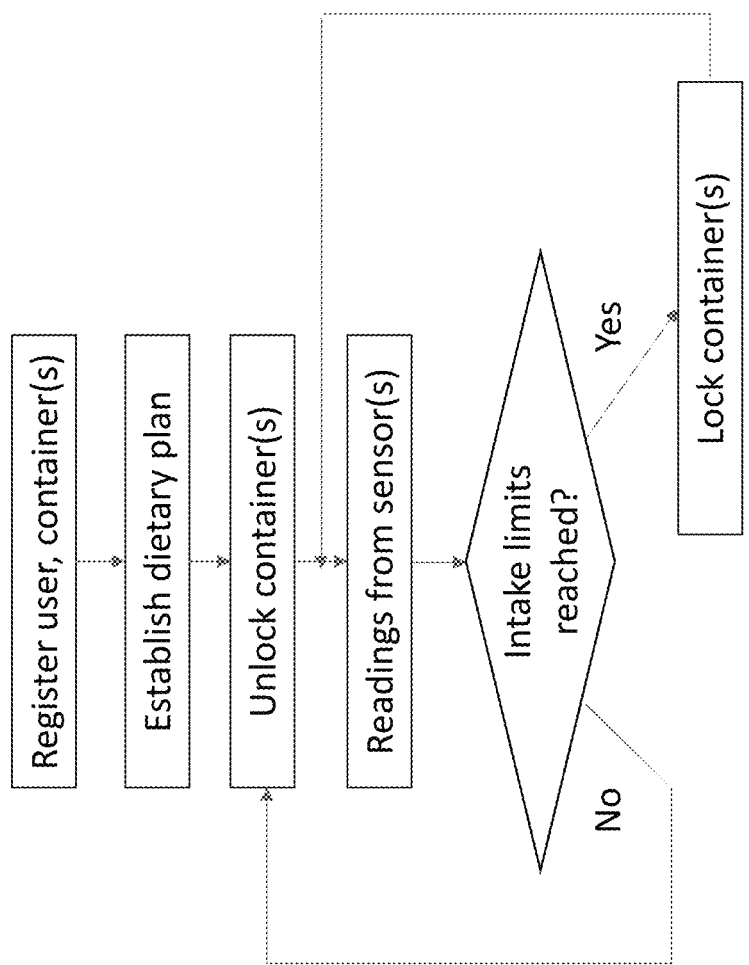
FIG. 3 is a flow chart with other exemplary logic for using the system of FIG. 1.
Figure 4:
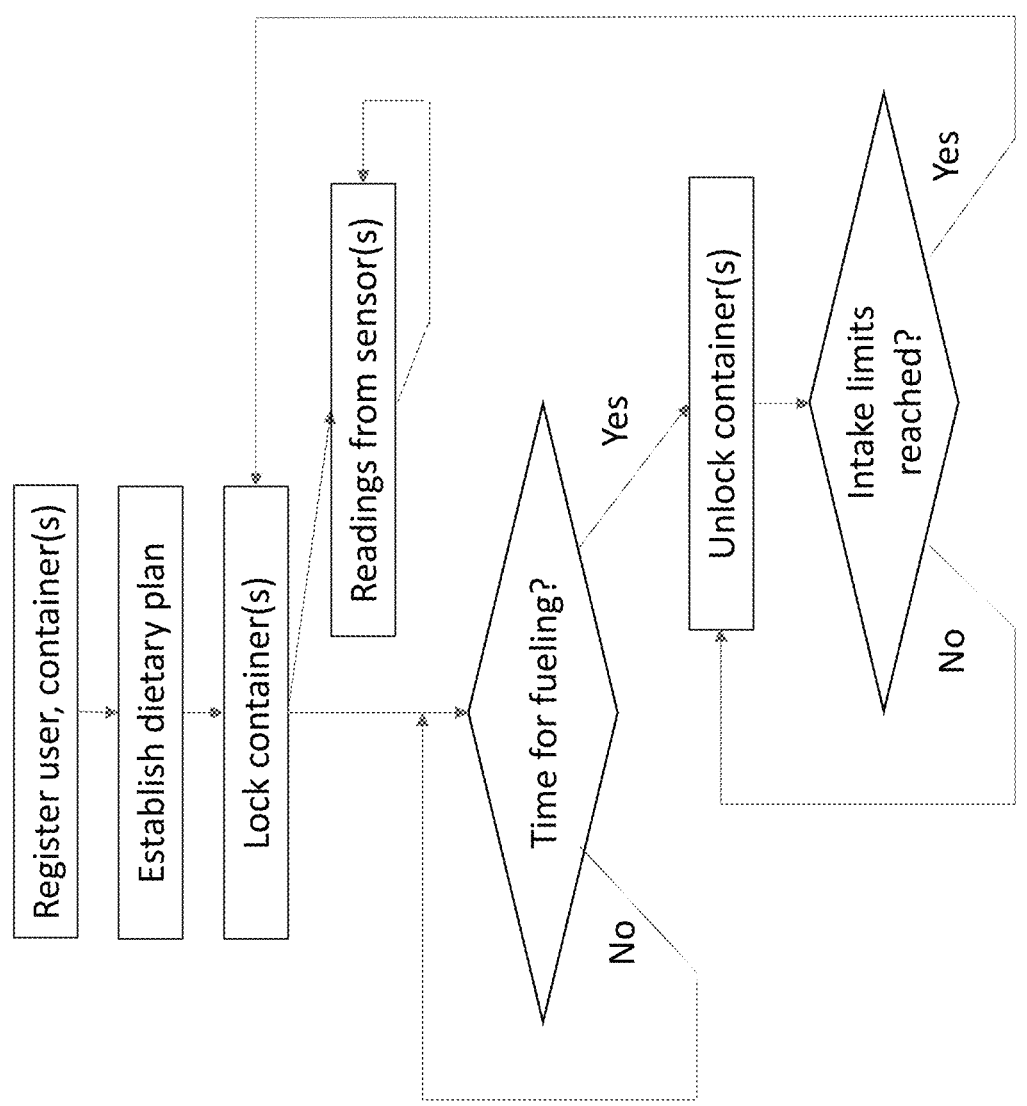
FIG. 4 is a flow chart with other exemplary logic for using the system of FIG. 1.

FIG. 2 through FIG. 4 illustrate exemplary logic for operating the system 10. A dietary plan may be established. The dietary plan may be established by default, by user 42 customization, and/or by a third-party (e.g., wellness coach, healthcare provider, personal trainer, etc.). The dietary plan may be established by user input at one or more of containers 16 (e.g., by way of the user interfaces 32), the wrist mounted devices 40, and/or the personal electronic devices 36.

Containers 16 associated with a user 42 may be registered or otherwise associated with the user 42 by way of the identifiers 31, by way of non-limiting example. For example, without limitation, the containers 16 may be scanned by the personal electronic device 36 and related or extracted information may be stored at the sever(s) 14.

Additional information may be subsequently associated with the various containers 16 (e.g., type of foodstuff), such as by way of the personal electronic devices 36, and stored at the sever(s) 14. Examples of such additional information include type of foodstuffs the user 42 intends to store in the containers 16, the types of meals the user 42 intends to use the container for, combinations thereof, or the like.

In other exemplary embodiments, without limitation, type of foodstuffs, amount of calories, type of meal information (e.g., breakfast, lunch, dinner, snacks) may be pre-associated with certain or all of the containers 16. For example, without limitation, upon registration or other association of the containers 16 with the user 42, such as by the identifier 31, the type of foodstuff may likewise be stored at the server(s) 14. By way of non-limiting example, the containers 16 may be designated as breakfast containers, lunch containers, dinner containers, snack containers, meal containers, starch containers, protein containers, vegetable containers, pizza container, ice cream container, chip container, meat container, combinations thereof, or the like.

An estimated amount of calories, in exemplary embodiments, without limitation, may be automatically associated with the container(s) 16 based on the type of container 16 and/or the type of foodstuff, or the like. The amount of calories consumed, in exemplary embodiments, without limitation, may be automatically counted as consumed upon access to, or unlocking of, such containers 16. For example, without limitation, 300 calories may be automatically denoted as consumed when a snack type container is opened, unlocked, or otherwise noted by the user 42 as being consumed (e.g., by way of the personal electronic device 30). Estimated amount of calories may be determined by container 16 size and/or type of foodstuff the container is configured or indicated to store.

By way of non-limiting example, the user 42 may indicate that an intermittent fueling program is desired whereby the user 42 is only eating during particularly scheduled times (e.g., 9 am to 9 pm, 10 am to 8 pm, etc.). As another example, without limitation, the user 42 may indicate that a caloric deficit plan is desired whereby the user 42 is consuming, for example, approximately 150 calories less per day than used. As yet another example, without limitation, the user 42 may indicate that a caloric surplus plan is desired whereby the user 42 is, for example, consuming approximately 250 calories more per day than used. Intermittent fueling may sometimes be referred to as intermittent fasting. Any time period, hours, or the like may be scheduled for intermittent fueling. Alternatively, or additionally, any amount of caloric surplus or deficit may be programmed.

The user 42 dietary plan and/or preferences may be communicated electronically to the server(s) 14 for storage, such as part of a user profile. The user 42 dietary plan and/or preferences, and/or operational programming for the containers 16 associated with the same, may be communicated electronically to the controllers 26 of the containers 16, such as by way of the server(s) 14, for storage and/or execution.

The controllers 26 may be configured to lock and unlock the containers 16, such as by way of the locking mechanisms 24, in accordance with the user 42 dietary plan and/or preferences.

With particular regard to FIG. 2, by way of non-limiting example, where an intermittent fueling plan is selected, the containers 16 may be programmed to unlock only during user specified times, and remain otherwise locked. The locking mechanism may be overridden by the user 42, such as by entry of a code.

With particular regard to FIG. 3, as another non-limiting example, locking and unlocking of the container 16 may be varied based on estimated caloric input and output relative to user goals (e.g., caloric surplus or deficit).

Readings from various sensors, including, but not limited to, the sensor(s) 28 of the container(s) 16, the smart utensils 34, personal electronic devices 36, wrist mounted devices 40, sensor(s) 102 of the footwear 38, combinations thereof, or the like, may be taken. The sensor measurements may be reported to the server(s) 14 for recording, such as in association with a user profile. The sensor readings may be taken periodically, continuously, randomly, combinations thereof, or the like. The sensor readings may be taken at a same or different time for each of the sensors. The sensor readings may be taken while other steps are taken. The sensor readings may be processed at the sensor(s) themselves and/or at the server(s) 14. The sensor readings may be reported electronically, such as by wireless communication device(s).

Sensor readings may be used to determine estimated caloric output and/or estimated caloric input for the user 42. By way of non-limiting example, estimated caloric output may be determined from the personal electronic devices 36, the wrist mounted devices 40, the sensor(s) 102 of the footwear 38, combinations thereof, or the like. More specifically, for example, without limitation, user 42 activity may be estimated by these sensors, such as based on perceived movement (e.g., activation of load cells in shoes, accelerometers in a smartphone, smartwatch, or other activity tracker, location tracking of smartphone, smartwatch, or other activity tracker, user 42 reported activities, temperature and/or moisture readings indicating physical activity, pedometer readings, combinations thereof, or the like).

User activity may, alternatively, or additionally, be self-reported by the user 42. For example, without limitation, individual activities may be reported (e.g., ran 6 miles, lifted weights for 20 minutes, performed yoga for 15 minutes, etc.). As another example, without limitation, estimated daily caloric activity may be provided. In exemplary embodiments, without limitation, a baseline estimate may be provided (as further discussed herein) and modified by caloric amount and/or general level of activity (e.g., sedentary, minimally active, very active, etc.).

By way of non-limiting example, estimated caloric input may be determined from the smart utensils 34 and/or wrist mounted devices 40 (e.g., indicating eating times, amount eaten), sensors 102 in the footwear 38 (e.g., load cells indicating increased weight forces 104 before and after eating), sensor(s) 28 in the container(s) 16 (e.g., amount of foodstuffs 22 removed), self-reported by users 42 (e.g., by way of personal electronic devices 36 and/or wrist mounted devices 40), combinations thereof, or the like.

The server(s) 14 and/or the controllers 26 may determine when to unlock and/or lock the containers 16 based on estimated caloric input and/or output relative to user 42 goals. For example, without limitation, the container 16 may remain unlocked until the user's 42 caloric intake goals are met. In exemplary embodiments, without limitation, the user's 42 caloric intake goals may be apportioned, such as into approximate thirds for three daily meals. Apportionment into any number of meals may be provided, and the caloric spread between meals may be the same or different (e.g., more calories allotted for lunch than breakfast). The user may be able to set a number of meals, time for meals, and/or manually adjust apportionment for meals, such as at the personal electronic device(s) 36 and/or the container(s) 16. The container 16 may be programmed to remain unlocked until an apportioned number of calories given the time of day and associated meal are reached (e.g., 600 calories between 7 am and 11 am, 800 between noon and 1 pm, 500 between 3 pm and 7 pm).

A baseline estimated caloric output may be determined, such as at the server(s) 14 based on user 42 provided details (e.g., height, weight, age, sex, combinations thereof, or the like). User current weight may be entered and/or determined from the sensors 102 in the footwear 38. The baseline estimated caloric output may be increased where activity is detected (e.g., the user 42 goes for a run). The amount of calories allotted for consumption may be varied accordingly and container 16 locking and unlocking may be updated accordingly, such as by way of the server(s) 14. For example, without limitation, where the user 42 is estimated to burn an additional 200 calories in a morning run, 200 additional calories may be allotted for the remaining day, next meal, or next day, such as on an apportioned basis, by addition of a mid-day snack, combinations thereof, or the like. Caloric surplus or deficits may be carried over into additional days.

Reminder notifications to eat more, less, and/or at particular times may be provided at the container 16, the personal electronic devices 36, the wrist mounted devices 40, combinations thereof, or the like, such as based on user 42 adherence to dietary plan goals.

In other exemplary embodiments, without limitation, the user 42 may specify a goal weight. User's 42 current weight may be entered and/or determined from the sensors 102 in the footwear 38. The sever(s) 14 may be configured to assign a dietary plan in accordance with the goal weight relative to current weight (e.g., caloric surplus or deficit). An amount of surplus or deficit to achieve the goal weight may be determined, such as by way of reference to one or more databases or maximum safety guidelines (e.g., no more than 500 calorie surplus/deficit per day). Weight measurements may be periodically provided or taken, such as by way of the sensors 102, and the container 16 programming may be updated accordingly. Notifications regarding the same (e.g., weight readings, progress updates, container 16 programming updates) may be provided to the user 42, such as at the container 16, personal electronic devices 36, wrist mounted devices 40, combinations thereof, or the like. In exemplary embodiments, without limitation, some or all of the containers 16 may remain locked or unlocked unless/until a particular weight is measured, such as by way of the sensors 102 in the footwear 38 by way of non-limiting example.

The logic of FIGS. 2 and 3 may be used together or separately. In exemplary embodiments, without limitation, intermittent fueling programs may be capped by caloric goals, such as illustrated in FIG. 4 by way of non-limiting example. For example, without limitation, the container(s) 16 may be programmed to lock or unlock based on time of day unless and until estimated net caloric surplus or deficits are reached, at which time the container 16 programming may be adjusted. For example, without limitation, the containers 16 may be programmed to be normally unlocked only between 10 am and 7 pm. However, if the user specifies a weight loss goal and the system 10 determines that the user 42 is in caloric surplus for the day (e.g., based on estimated caloric input and estimated caloric output as shown and/or described herein), the containers 16 may be prematurely locked, such as until the system 10 determines that the dietary goals are met. As another example, without limitation, the containers 16 may be programmed to be normally locked between 8 pm and 8 am the following day. However, if the user specifies a weight gain goal and the system 10 determines that the user 42 is in caloric deficit for the day (e.g., based on estimated caloric input and estimated caloric output as shown and/or described herein), the containers 16 may be left unlocked, such as until the system 10 determines that the dietary goals are met. In this fashion, the caloric goals may override the intermittent fueling program to ensure that the user remains in adherence with overall dietary goals (e.g., caloric deficit and weight loss, caloric surplus and weight gain, and/or caloric balance). Notifications regarding the same, or other information, may be provided to the user 42, such as at the container 16, personal electronic devices 36, wrist mounted devices 40, combinations thereof, or the like.

Any of the steps shown and/or described may be omitted and/or performed in any order.

Figure 5A:
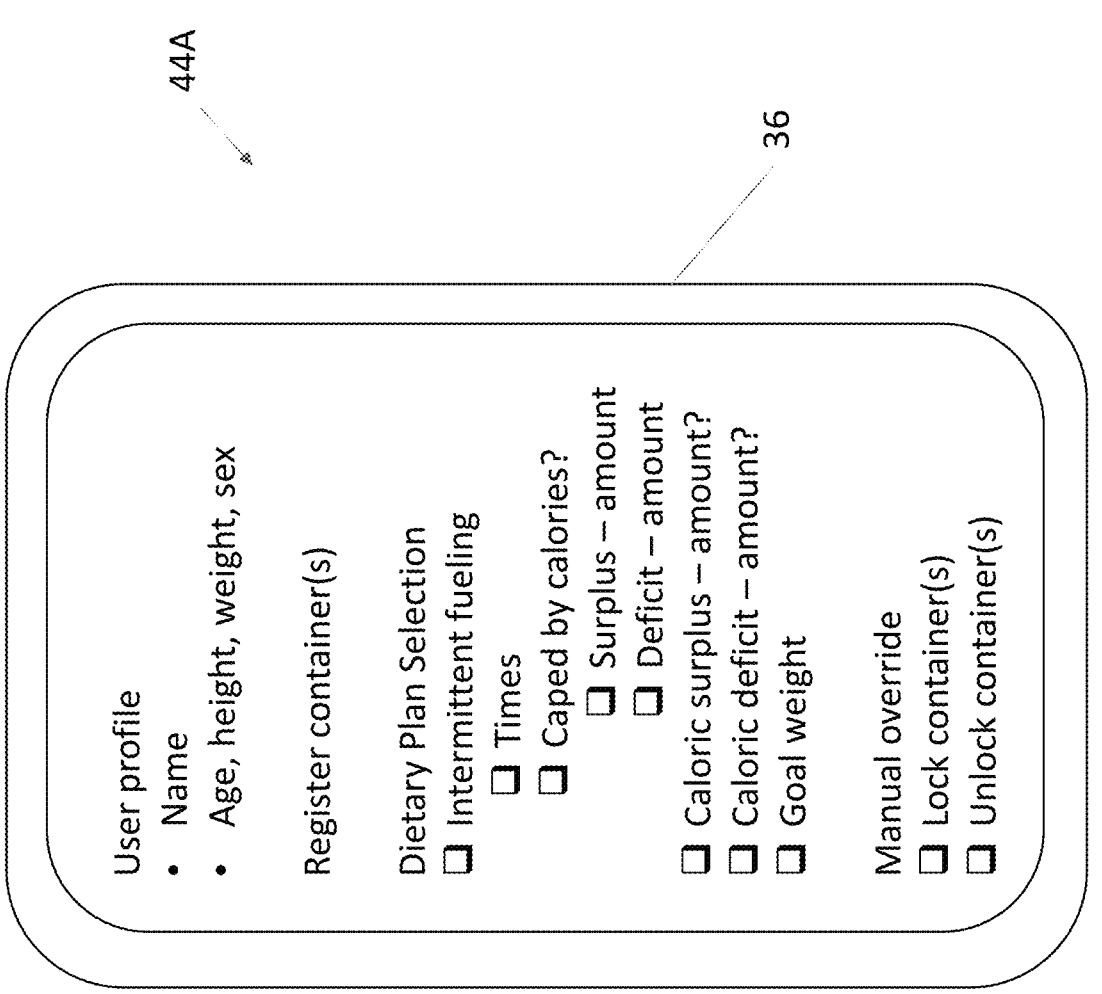
FIG. 5A illustrates an exemplary user interface for an application for operating the system of FIG. 1.
Figure 5B:
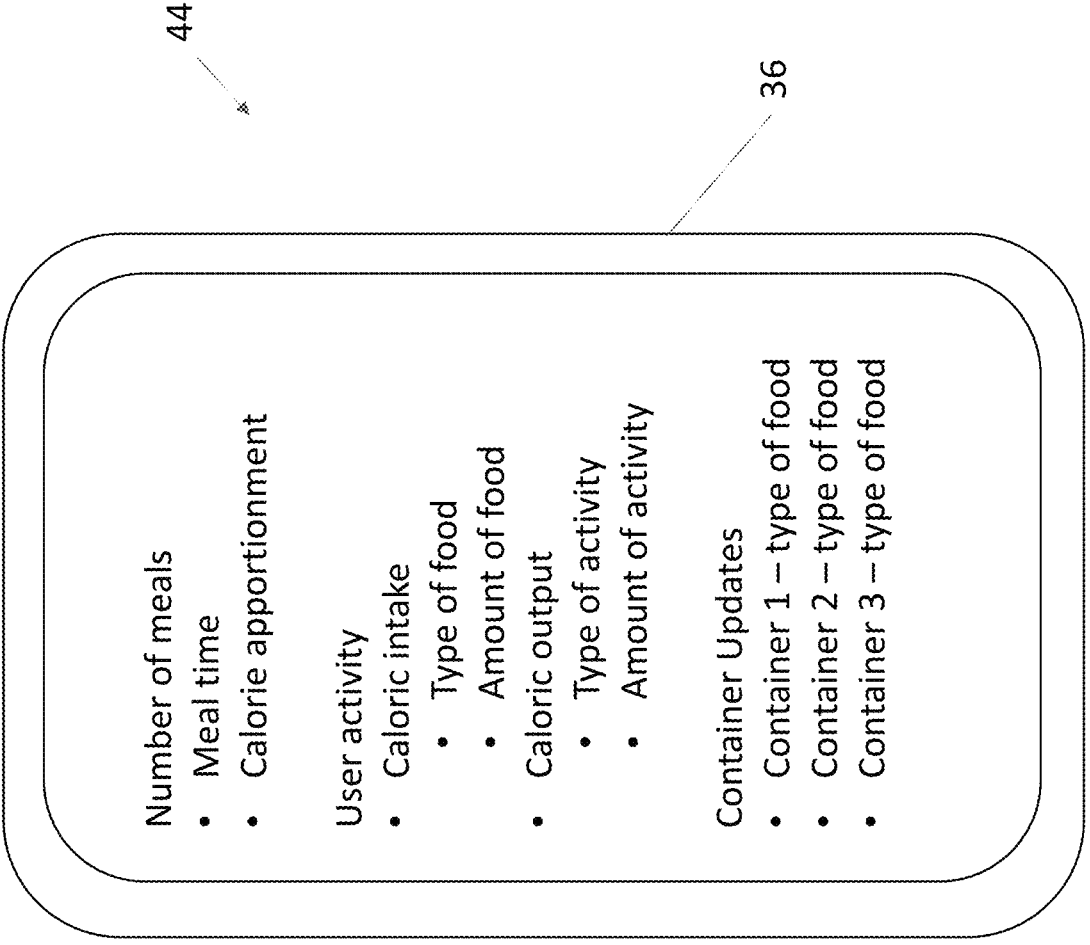
FIG. 5B illustrates another exemplary embodiment of the user interface of FIG. 5A.

FIG. 5A and FIG. 5B illustrate exemplary user interfaces 44A, 44B for the application. The type, arrangement, and kind of information and options illustrated are merely exemplary and are not intended to be limiting. Any type or kind of information provided in any arrangement or format may be utilized. The user interface 44 may be separated into multiple pages, prompts, or sections. While shown as on the personal electronic device 36, the user interface 44 may be provided at other components, such as the containers 16 and/or wrist mounted device 40.

User profile information may be entered (e.g., name, age, height, weight, sex). Dietary plan selections may be made (e.g., intermittent fueling, including time selection, capped by calories, caloric surplus and amount, caloric deficit and amount, weight goal).

Manual overrides, such as to lock or unlock the containers 16, may be provided. Manual overrides may be made by user selection and may require entry and verification of a code. Manual overrides may, alternatively, or additionally, be made by use of hardware such as a key, RFID tag, or the like.

Caloric input and/or caloric output may be manually entered. Such entries may be made by specifying a type and/or amount of foodstuff 22 and/or a type and/or amount of activity. Estimated caloric input and output may be determined, such as by way of reference to one or more databases or electronically stored tables associating foodstuff 22 types, foodstuff 22 amounts, activity types, and activity durations with calories. Types of foodstuff 22 placed in the containers 16 may be entered at the interface 44B. In this manner, by way of example, that estimated caloric intake may be determined, such as based on an entered type of foodstuff 22 and measured amount of foodstuff 22 removed from the containers 16. Numbers of meals and apportionment information may be entered. Other user preferences may be entered. If preferences are not entered, certain default configurations may be utilized.

Any embodiment of the present invention may include any of the features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention.

Certain operations described herein may be performed by one or more electronic devices. Each electronic device may comprise one or more processors, electronic storage devices, executable software instructions, combinations thereof, and the like configured to perform the operations described herein. The electronic devices may be general purpose computers or specialized computing devices. The electronic devices may comprise personal computers, smartphone, tablets, databases, servers, or the like. The electronic connections and transmissions described herein may be accomplished by wired or wireless means. The computerized hardware, software, components, systems, steps, methods, and/or processes described herein may serve to improve the speed of the computerized hardware, software, systems, steps, methods, and/or processes described herein.

What is claimed is:

1. A container for facilitating dietary plan adherence, said container comprising:

an access panel moveable between an opened position and a closed position;

a locking mechanism configured to selectively secure the access panel in the closed position; and a controller configured to:

receive user input regarding dietary plan preferences and operate said locking mechanism in accordance with said user input; and command said locking mechanism to unlock upon receipt of a manual override.

2. The container of claim 1 wherein:

said access panel comprises a lid configured for hinging movement between said closed position and said opened position.

3. The container of claim 1 further comprising:

a user interface configured to receive said user input.

4. The container of claim 1 further comprising:

a network communications device configured to receive said user input by way of a remote electronic device.

5. The container of claim 1 wherein:

said dietary plan preferences comprise eating hours and non-eating hours;

said controller is configured to operate said locking mechanism to secure said access panel in said closed position during said non-eating hours; and said controller is configured to operate said locking mechanism to permit movement of said access panel into said opened position during said eating hours.

6. The container of claim 1 further comprising:

one or more sensors configured to provide weight readings for said container, wherein:

said user input comprises a type of stored foodstuff;

said dietary plan preferences comprise a desired daily caloric intake amount;

said controller is configured to determine an available caloric value of removed foodstuffs from said containers from the weight readings and the type of foodstuff indicated in the user input;

said controller is configured to operate said locking mechanism in a locked configuration where the available caloric value of the removed foodstuff for a given day exceeds said desired daily caloric intake amount; and said controller is configured to operate said locking mechanism in an unlocked configuration where the available caloric value of the removed foodstuff for the given day falls below said desired daily caloric intake amount.

7. The container of claim 6 further comprising:

a network communications device configured to receive activity data from one or more of a smartphone, smartwatch, and activity tracker, wherein said controller is configured to automatically increase the desired daily caloric intake amount upon receipt of said activity data indicating caloric burning activity.

8. The container of claim 6 further comprising:

dividers partitioning an interior compartment into multiple spaces, wherein each of said one or more sensors is associated with a respective one of said multiple spaces, and wherein said user input comprises a type of stored foodstuff for each of said multiple spaces and said controller is configured to determine the available caloric value of the removed foodstuffs on a cumulative basis based on individual determinations for each of the types of foodstuffs stored at each of the multiple spaces.

9. A system for facilitating dietary plan adherence, said system comprising:

one or more containers, each comprising:

a lid;

a locking mechanism for selectively locking the lid in a closed position;

a sensor configured to provide a weight reading for the container;

a controller in electronic communication with said sensor and said locking mechanism; and a network communication device in electronic communication with said controller;

one or more servers comprising software instructions, which when executed, configure one or more processors to:

generate one or more prompts at a personal electronic device for a user to provide dietary goal information;

generate one or more prompts at the personal electronic device for the user to provide foodstuff information for each of said one or more containers;

receive activity data from one or more of: the personal electronic device and an activity tracker associated with the user;

receive said weight readings from said one or more containers; and operably control said locking mechanism of each of said one or more containers based, at least in part on, said dietary goal information, said foodstuff information, said weight readings, and said activity data.

10. The system of claim 9 further comprising:

one or more databases comprising caloric values by weight of various foodstuffs, caloric values by time of various activities, and baseline caloric burning values;

additional software instructions stored at said one or more servers, which when executed, configure said one or more processors to:

determine an estimated number of consumed calories based on changes in said weight readings and an indicated type of the various foodstuffs for each of said containers;

determine an estimated amount of burned calories based on said activity data and one of the baselines; and modify operations of said locking mechanism of said one or more containers based on a net value of the estimated number of consumed calories and the estimated amount of burned calories for a given time period relative to said dietary goal information.

11. The system of claim 10 wherein:

said dietary goal information indicate a desire for any one of: caloric surplus, caloric deficit, or caloric maintenance;

said modified operations of said locking mechanism of said one or more containers comprise locking said locking mechanism of said one or more containers earlier than otherwise scheduled where said net value is positive and said dietary goal information comprises caloric deficit or caloric maintenance;

said modified operations of said locking mechanism of said one or more containers comprise unlocking said locking mechanism of said one or more containers earlier than otherwise scheduled where said net value is negative said dietary goal information comprises caloric maintenance; and said modified operations of said locking mechanism of said one or more containers comprise unlocking said locking mechanism of said one or more containers earlier than otherwise scheduled where said net value is negative and below a predetermined amount and said dietary goal information comprises caloric deficit of the predetermined amount specified by user input.

12. The system of claim 10 wherein:

the given time period comprises a 24 hour period;

the baselines are specific to age, height, weight, and sex; and said one or more servers comprise additional software instructions, which when executed, configure said one or more processors to generate one or more prompts at the personal electronic device for the user to provide height, weight, and sex information.

13. The system of claim 10 wherein:

said dietary goal information indicates an intermittent fueling program capped by a caloric deficit amount;

said operations of said locking mechanism normally include scheduling unlocking of said one or more containers based on said intermittent fueling program;

said modified operations of said locking mechanism of said one or more containers comprise locking said locking mechanism of said one or more containers for a period of time longer than scheduled where said net value is positive or negative by an amount less than said caloric deficit amount.

14. The system of claim 13 wherein:

said modified operations of said locking mechanism of said one or more containers comprise unlocking said locking mechanism of said one or more containers for a period longer than scheduled where said net value is negative by an amount greater than said caloric deficit amount.

15. The system of claim 9 wherein:

said activity tracker is selected from the group consisting of: a smartphone, a smartwatch, footwear or an insole with an integrated sensor, and a smart utensil.

16. The system of claim 15 wherein:

said activity tracker comprises an insole;

said integrated sensor comprises a temperature sensor; and said insole comprises a thermal gel in contact with said temperature sensor.

17. A method for facilitating dietary plan adherence, said method comprising:

generating prompts at a personal electronic device for a user to provide dietary goal information;

generating prompts at the personal electronic device for the user to provide foodstuff information for each of a plurality of containers;

electronically and wirelessly receiving activity data from one or more of: the personal electronic device and an activity tracker associated with the user;

electronically and wirelessly receiving weight readings from sensors of said containers; and automatically and electronically controlling operations of locking mechanisms of said containers based, at least in part on, said dietary goal information, said foodstuff information, said weight readings, and said activity data.

18. The method of claim 17 further comprising:

generating prompts at the personal electronic device for the user to provide age, height, weight, and sex;

automatically and electronically determining a baseline metabolic rate based on said age, height, weight, and sex;

automatically and electronically determining an estimated number of consumed calories based on changes in said weight readings and an indicated type of foodstuff for each of said containers;

automatically and electronically determining an estimated amount of burned calories based on said activity data and the baseline metabolic rate; and modifying operations of said locking mechanism of said containers based on a net value of the estimated number of consumed calories and the estimated amount of burned calories for a given time period relative to said dietary goal information.

19. The method of claim 18 further comprising:

receiving user input regarding a calorie capped intermittent fueling program as part of said dietary goal information;

scheduling unlocking and locking of said one or more containers based on said calorie capped intermittent fueling program;

modifying said schedule such that said containers are locked for a longer period of time where said net value is positive or negative by an amount less than said caloric deficit amount; and modifying said schedule such that said containers are unlocked for a longer period of time where said net value is negative by an amount greater than said caloric deficit amount.

* * * * *